United States Patent [19]
Curtiss

[11] 3,939,839
[45] Feb. 24, 1976

[54] RESECTOSCOPE AND ELECTRODE THEREFOR

[75] Inventor: Lawrence E. Curtiss, Stamford, Conn.

[73] Assignee: American Cystoscope Makers, Inc., Stamford, Conn.

[22] Filed: June 26, 1974

[21] Appl. No.: 483,117

[52] U.S. Cl. ................ 128/303.15; 128/7; 128/407
[51] Int. Cl.² ......................................... A61B 17/32
[58] Field of Search..... 128/303.15, 303.14, 303.13, 128/303.17, 4, 7, 240, 241, 404, 405, 407–409

[56] References Cited
UNITED STATES PATENTS

| | | | |
|---|---|---|---|
| 1,303,135 | 5/1919 | Wappler | 128/7 |
| 2,028,635 | 1/1936 | Wappler | 128/303.14 |
| 2,029,487 | 2/1936 | Kleine | 128/303.14 |
| 2,038,393 | 4/1936 | Wappler | 128/7 |
| 3,294,085 | 12/1966 | Wallace | 128/303.15 |
| 3,752,159 | 8/1973 | Wappler | 128/303.15 |
| 3,835,842 | 9/1974 | Iglesias | 128/303.15 |
| 3,850,175 | 11/1974 | Iglesias | 128/303.15 |

FOREIGN PATENTS OR APPLICATIONS

| | | | |
|---|---|---|---|
| 1,548,389 | 10/1968 | France | 128/303.15 |

Primary Examiner—Robert W. Michell
Assistant Examiner—Lee S. Cohen
Attorney, Agent, or Firm—John A. Howson, Esq.

[57] ABSTRACT

The disclosed apparatus includes a resectoscope with a novel working element stem, a novel cutting electrode for use with the stem and novel electrical features including a dielectric moving block element for reciprocating the electrode. The stem portion of the working element has a telescope channel member with a central axis and a pair of cutting electrode guide channel members spaced apart and mounted on opposite sides of the telescope channel member above its central axis. The cutting electrode consists of a single length of electrically conductive wire with a loop portion in the middle of the wire and a pair of substantially straight, flexible, parallel, spaced apart insulation covered arms having similar lengths and extending rearwardly from the loop in the same direction. The arms of the electrode are inserted within the cutting electrode channel members in the working element stem. The size and number of electrically conductive exterior parts of the instrument are minimized and the capacitive and ohmic coupling of these parts to the active conductors is minimized to reduce the chance of accidental burns to the doctor or the patient.

19 Claims, 14 Drawing Figures

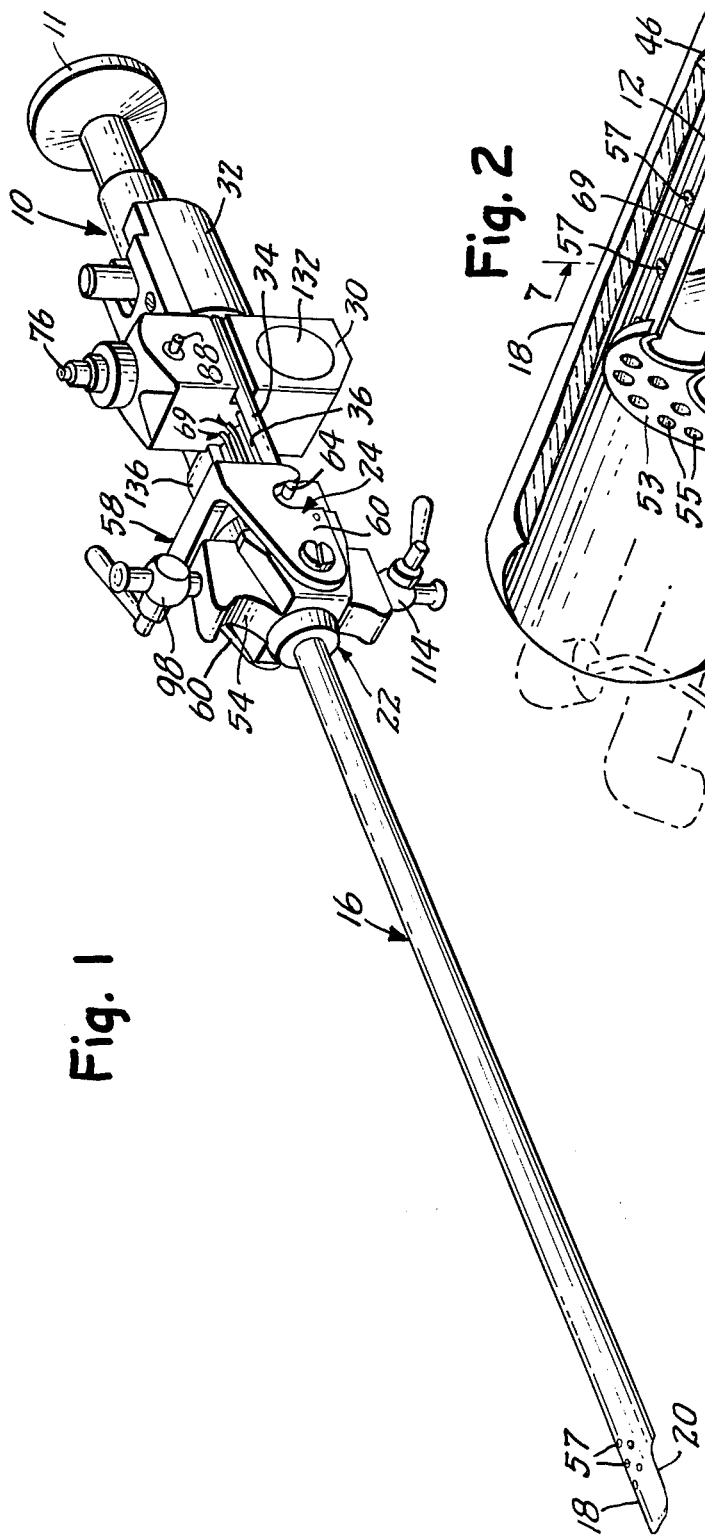
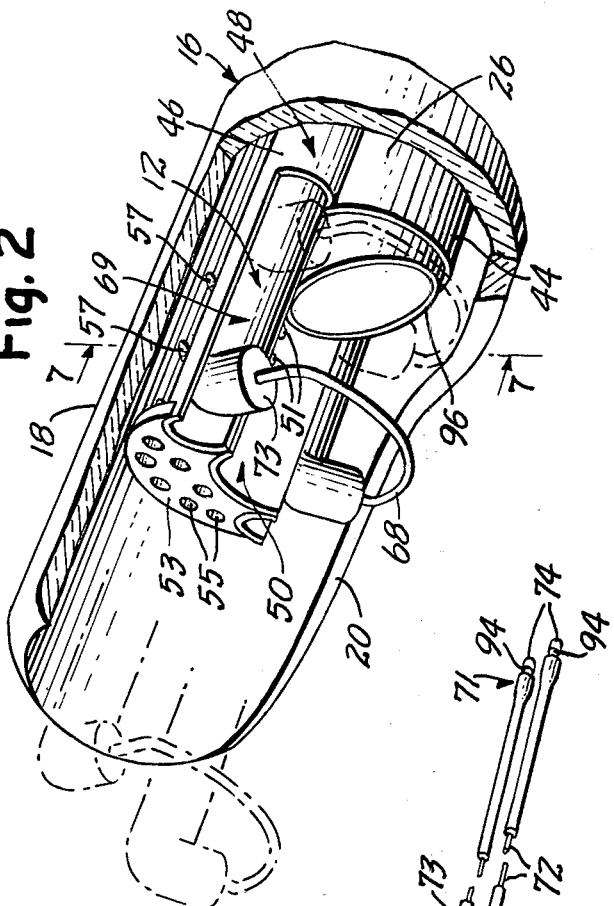
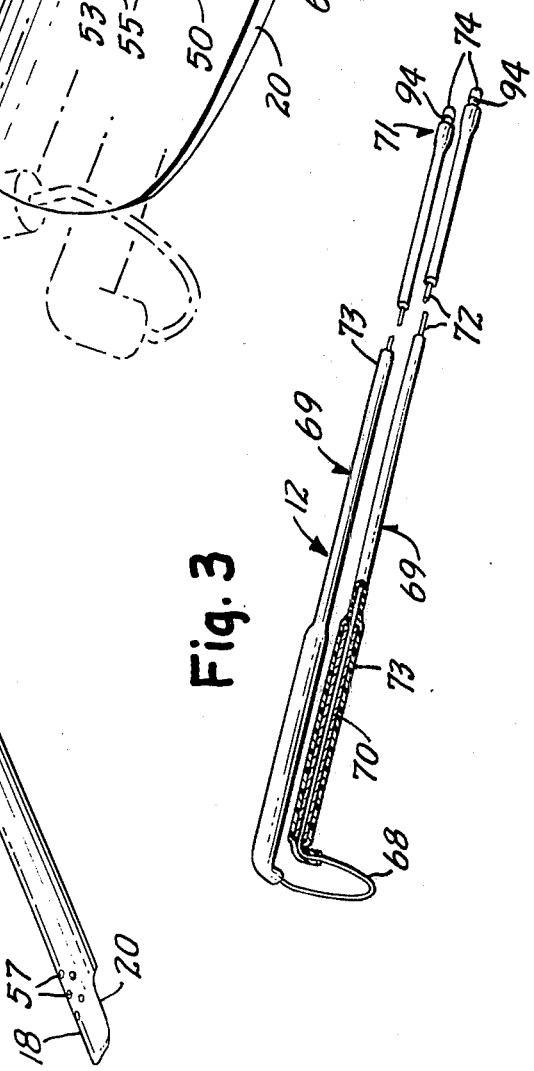
Fig. 1
Fig. 2
Fig. 3

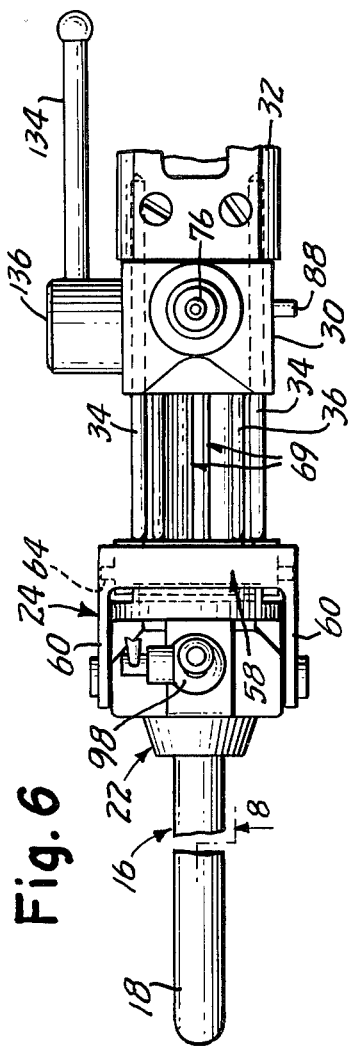
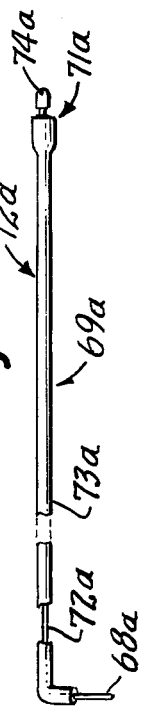
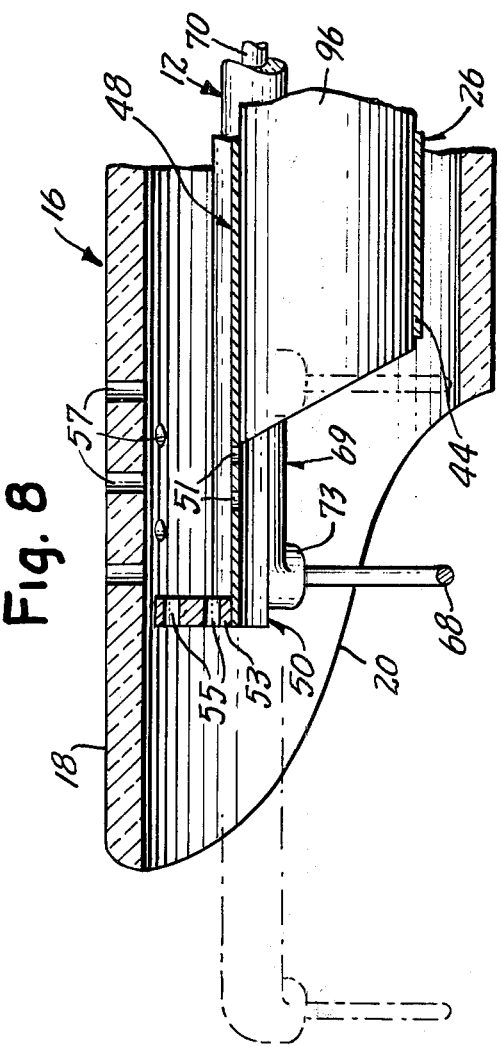
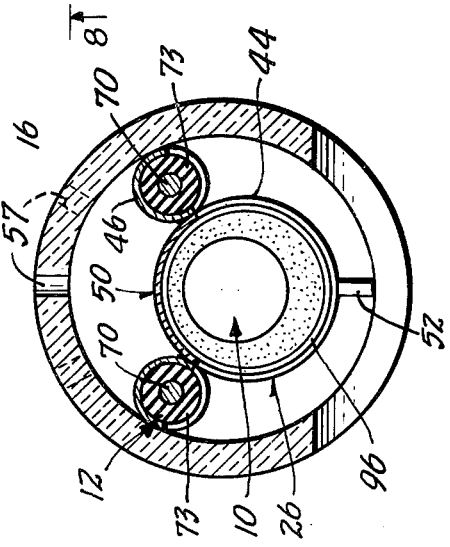
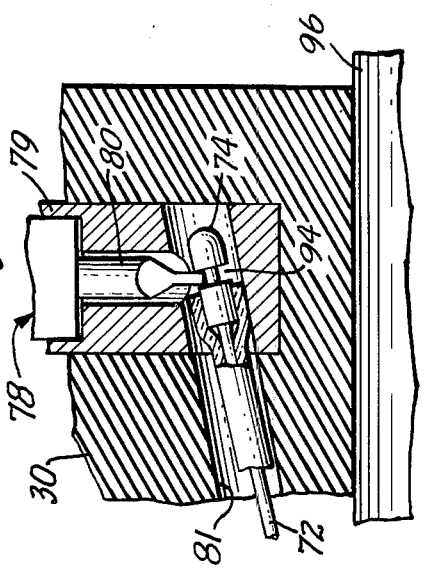

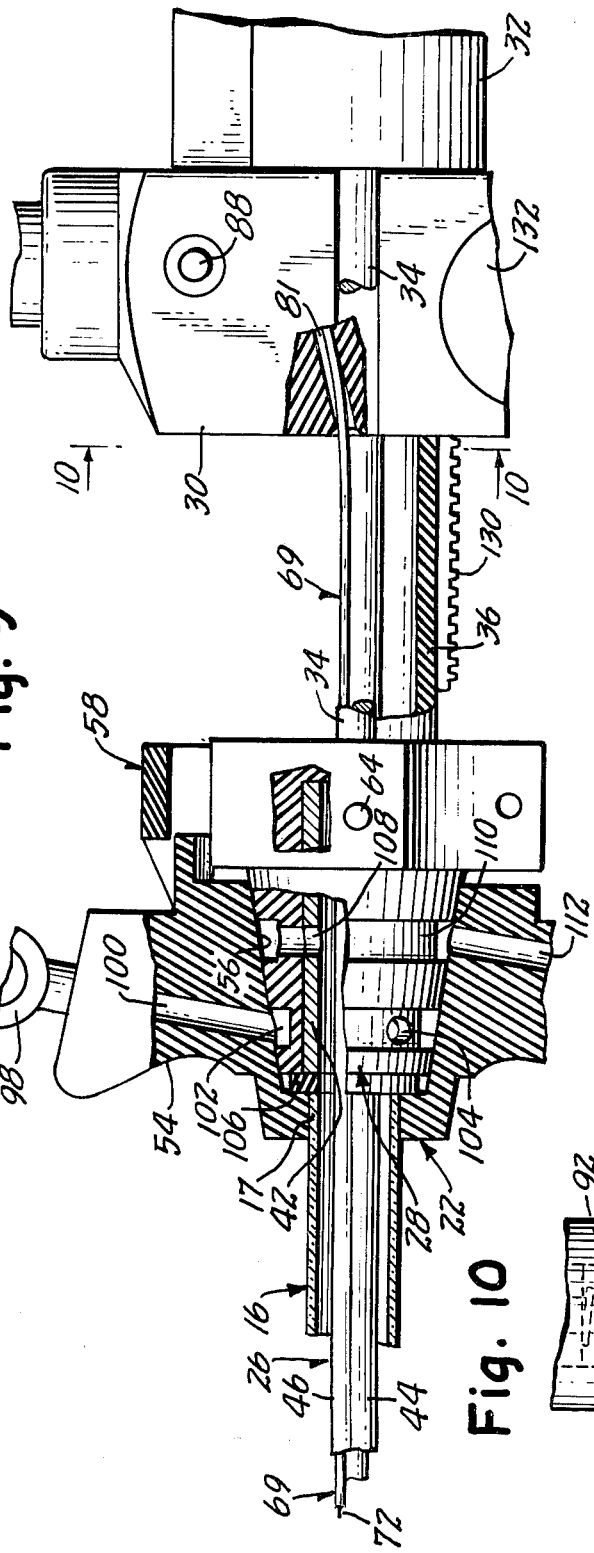
Fig. 9
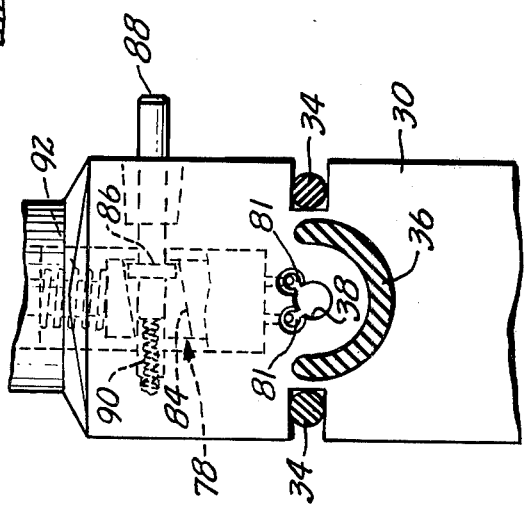
Fig. 10
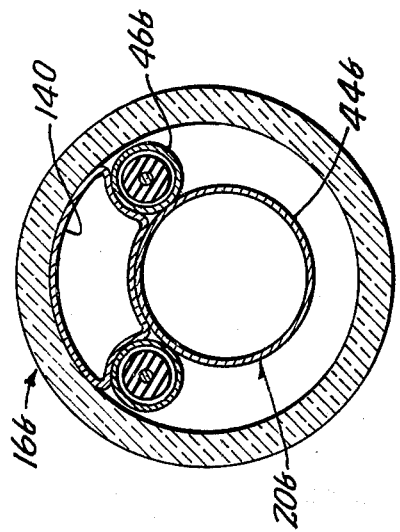
Fig. 11
Fig. 12

RESECTOSCOPE AND ELECTRODE THEREFOR

BACKGROUND OF THE INVENTION

This invention relates to resectoscopes and more particularly to an improved resectoscope and a novel cutting electrode for use with it.

Resectoscopes are surgical endoscopes for transurethral resection of the prostate gland or bladder growths and for the coagulation of bleeding vessels in the area of the prostate and bladder. The basic components of a resectoscope are a telescope, a working element assembly, a cutting electrode and a sheath. The sheath portion of the instrument is inserted in the urethra using an obturator which is then removed from it in order that the stem portion of the working element assembly with the telescope and cutting electrode can be mounted in the sheath. The telescope, typically about 4 mm. in diameter and about a foot long, lies in a snug yet slidable relationship in a channel in the stem portion of the working element assembly. It has a viewing system with an eyepiece at its proximal end and an objective lens at its distal end as well as means, such as a bundle of light carrying fibers or an incandescent lamp, for illuminating the telescope's field of view. The cutting electrode (typically formed of insulated tungsten wire between about 0.010 to 0.018 inches in diameter) is also carried by the working element assembly inside the sheath and has an uninsulated or bare arcuate cutting loop portion which is reciprocated forward and back through the sheath's fenestra in front of and within the field of view of the telescope.

The mechanical arrangement for reciprocating the electrode varies in different resectoscopes and forms no part of the present invention. Some instruments use a rack and pinion, others a spring and thumb control, while others use a fixed thumb position and move the electrode with the fingers via a movable block in the working element assembly. Cutting is accomplished by reciprocating the electrode while applying electrical high frequency currents to the electrode at voltages of between about 250 volts to about 4,000 volts or more at frequencies of from about 0.4MHz to about 3MHz. To facilitate clearing the telescope's field of view of the blood and other debris which tend to obstruct the doctor's view during resection, clear irrigation fluid is typically passed through the sheath and in front of the telescope's objective lens. In some resectoscopes a drain is also provided to allow continuous irrigation fluid flow through the sheath both in and out of the bladder.

Heretofore, insulation breakdown and capacitive coupling in resectoscopes in which the electrode is operated at the above indicated voltages and frequencies, has often caused accidental electrical burns to the doctor using the instrument and to the patient in whom the instrument is being used. Further, without an expensive stabilizer structure, prior art cutting electrodes used in such instruments lack adequate rigidity against upward and lateral deflection created by forces to which the electrode is subjected during resection. Without adequate rigidity, the extended electrode may be deflected out of the field of view, and the retracting electrode can be pushed out of alignment with the sheath, frequently contacting and burning the sheath's lower lip or causing electrical arcing between the electrode and the telescope. This often results in expensive damage to the latter and can cause termination of the surgical procedure. In addition, with prior art resectoscopes, the field of view is too often obscured by bubbles, blood and other debris which is not swept away by adequate irrigation flow, thus making uninterrupted operation of the instrument difficult.

One object of the invention, therefore, is to provide a new resectoscope which has substantially higher electrical safety than prior art devices and hence is less likely to cause accidental burns to either doctor or patient.

Another object is to provide a resectoscope with a high flow capacity continuous irrigation system which maintains a clearer visual field in front of the telescope and permits longer periods of uninterrupted operation of the instrument than heretofore.

Still another object is to provide a simple novel cutting electrode for use in the improved resectoscope.

A further object is to provide a novel resectoscope in which the cutting electrode loop is more adequately stabilized and supported in its path of travel than in prior art devices.

A still further object is to provide a novel resectoscope which maximizes the space inside the sheath available for irrigation fluid flow.

Yet another object is to provide a resectoscope in which: (a) the telescope is more effectively insulated from the ground or patient plate potential; (b) the size and number of exterior electrically conductive parts of the resectoscope are minimized; and (c) the capacitive coupling of these parts to the active conductors is reduced.

Further, other and additional objects and advantages of the invention will become apparent from the summary and detailed description of the invention which follow, as well as from the drawings and the appended claims.

Summary Of The Invention

In one aspect, the invention comprises a working element assembly for use in a resectoscope having a sheath, said assembly including a stem portion for insertion within the sheath, and having a telescope channel member with a central axis and a pair of parallel cutting electrode guide channel members spaced apart and sealingly mounted along the length of the telescope channel member on opposite sides thereof above its central axis. In the preferred embodiment, the telescope channel member and electrode guide channel members are integral with each other so no fluid can pass between them and the radial peripheries of the guide channel members sealingly engage the sheath wall in a snug yet slidable relationship so the stem alone divides the space inside the sheath into a space above and a space below the electrode guide channel members and no fluid will pass by them from one space to the other. The irrigation fluid conduits are formed between the stem and the sheath with the drainage conduit being defined by either the upper or the lower of these two spaces. The irrigation fluid inflow conduit, naturally, is defined by the one of these two spaces not used as the drainage conduit.

In a second embodiment, the radial peripheries of the cutting electrode guide channel members do not engage the interior wall of the sheath. Instead, the working element stem includes a cover which fits snugly and fixedly over and against the peripheries of these members. This cover also engages the sheath in a snug but slidable relationship to allow the stem to be inserted into and removed from the sheath. In this embodiment, the space between the cover, the electrode guide channel members and the upper portion of the telescope channel member defines a conduit between them which can be used for irrigation fluid drainage or inflow purposes.

In a third embodiment, the working element stem includes a complete conduit mounted on top of the telescope channel and between guide channel members of the stem. In this third embodiment, the interior area of this conduit, which also can be used as an irrigation fluid drain or inflow conduit, is somewhat reduced, due to the thickness of the material forming it. There is only a single thickness of such material in the second embodiment due to the cover itself and no conduit forming material between the stem and the sheath in the preferred embodiment. The preferred embodiment, therefore, maximizes the cross sectional area between the sheath and the working element stem available for bringing in and draining the irrigation fluid.

Another advantage of the preferred embodiment is that the upper conduit, formed between the stem and the sheath, is cleaned more easily (when the stem and the sheath are separated) than when the stem is covered or a fully enclosed conduit is provided.

In another aspect, the invention comprises terminating the lower portion of the working element stem at a point within the sheath while extending its upper portion (including the upper portion of the electrode guide channel members and the upper portion of the telescope channel member between them), forwardly within the sheath. This upper portion of the stem comprises a roof which is extended in the forward direction a distance through the sheath above the sheath's window or fenestra through which the cutting electrode does its cutting. This extension serves two functions and provides two fundamental advantages. First, it moves the irrigation fluid conduit above the telescope to a point in front of and above the distal end of the telescope. When used as a drainage conduit, this helps create and maintain a flow of fresh clear irrigation fluid through the telescope's field of view to keep it clear for easy viewing of the area of interest to the doctor. Secondly, by extending part of the cutting electrode channel members to a point forward of the telescope's objective lens, a rigid non-moving support is provided for holding the cutting electrode against upward and lateral movement throughout at least a portion of its path of travel forward and back in front of the telescope.

Still another aspect of the invention comprises providing a simple cutting electrode for use with the improved resectoscope. The electrode comprises a single length of electrically conducting wire (preferably tungsten) having a conventional exposed arcuate cutting loop portion in the middle of the wire and two novel substantially straight flexible parallel spaced apart arms covered with insulation and extending rearwardly from the loop in the same direction throughout the remaining length of the electrode. Each arm terminates in a free end portion which preferably includes a quick disconnect male electrical terminal. The insulation covering the wire is preferably made from a known fluorocarbon resin (comprising a group of synthetic resins based on tetrafluoroethylene polymers) which is available from Dupont De Nemours & Company under the trademark Teflon-FEP. The insulation encapsulates the wire arms with a thickness of preferably at least about 0.015 inches. The preferred embodiment of the electrode according to the invention also includes a stiffened wire portion on each arm extending rearwardly from the loop portion of the electrode a distance longer than the electrode's length of travel when reciprocated forward and back its full distance in the instrument. The addition of such a feature helps ensure rigidity of the loop portion of the electrode when it is reciprocated beyond the roof portion of the working element stem and pressure is exerted against the loop in the lateral or vertical directions.

A further aspect of the invention includes forming the moving block portion of the working element assembly and other exterior and interior parts of the instrument from a known physically strong dielectric material such as acetal resin. This material is available from the DuPont de Nemours & Company under the trade-mark DELRIN. Upwardly sloping channels are formed in the moving block for the free ends of the electrode arms to keep the electrical connections of the arms far enough away from the telescope shaft, which is made of metal, to reduce the risk of dielectric breakdown in the block. In addition, to the extent possible all other parts of the resectoscope which are exposed to contact by the doctor or patient are formed of dielectric material. Necessary external parts which are capable of conducting electricity have a minimum of conductive interconnections and are made as small as possible. Further, they are preferably spaced as far as practicable from the active conductors to reduce the capacitive coupling to such conductors to below about 4 pico farads and preferably below about 2 pico farads. The ohmic coupling of these parts should be minimized by maintaining the resistance between them and the active conductors at a level of not less than about 25,000 ohms. As far as possible, the metal shaft of the telescope is isolated from all conducting materials which assume a ground or patient plate potential. Hence, the telescope can assume high voltage without a substantial flow of current to the telescope shaft which can damage it severely.

A still further aspect of the invention includes providing one or more feet on the exterior of the telescope channel portion of the stem spaced a distance rearwardly from the distal end of its bottom portion. This foot or feet serve to support the distal end of the stem from the bottom of the sheath. In the preferred embodiment, this helps maintain portions of the cutting electrode guide channel members of the stem tightly sealed against the sheath to minimize or prevent irrigation fluid leakage between the irrigation fluid supply and drainage conduits. The foot or feet also space the bottom portion of the stem far enough away from the sheath to allow the fluid to flow past the distal end of the telescope smoothly.

BRIEF DESCRIPTION OF THE DRAWINGS

FIG. 1 is a perspective view of the preferred embodiment of a resectoscope according to the invention.

FIG. 2 is a perspective view of from underneath, partially cut away, of the distal end portion of the embodiment of FIG. 1.

FIG. 3 is a perspective view of the preferred embodiment of a cutting electrode according to the invention.

FIG. 6 is a plan view in elevation of a portion of the embodiment of FIG. 1.

FIG. 7 is a cross sectional view of the preferred embodiment of the invention taken along lines 7—7 of FIG. 2.

FIG. 8 is a vertical cross section view in elevation of the distal end of the preferred embodiment of the resectoscope, taken along line 8—8 of FIG. 6.

FIG. 9 is a vertical elevation view of the main sections of the working element assembly and sheath portions of the embodiment of FIG. 1, shown partially cut away and partially in section to illustrate the irrigation fluid inflow and drainage conduit connections.

FIG. 10 is a profile view in vertical elevation of the moving block portion of the working element assembly taken along lines 10—10 of FIG. 9 with the electrical connection mechanism inside it partially shown in phantom.

FIG. 11 is a cross sectional vertical elevation view of the second embodiment of the working element stem portion of a resectoscope according to the invention taken through the middle of the sheath and showing a cover over the cutting electrode guide channel members.

FIG. 12 is a vertical cross sectional elevation view similar to that of FIG. 11, showing a third embodiment of the working element stem portion of a resectoscope according to the invention in which the irrigation fluid drain conduit defines a tube mounted on the upper surface of the telescope channel member between the cutting electrode guide channel members.

FIG. 13 is a vertical elevation view of a second embodiment of a cutting electrode according to the invention.

FIG. 14 is a blow up vertical elevation view in partial cross section illustrating the quick release electrical connections in the moving block for the male terminals on the free ends of the electrode arms.

DETAILED DESCRIPTION OF THE INVENTION

Figure 4:
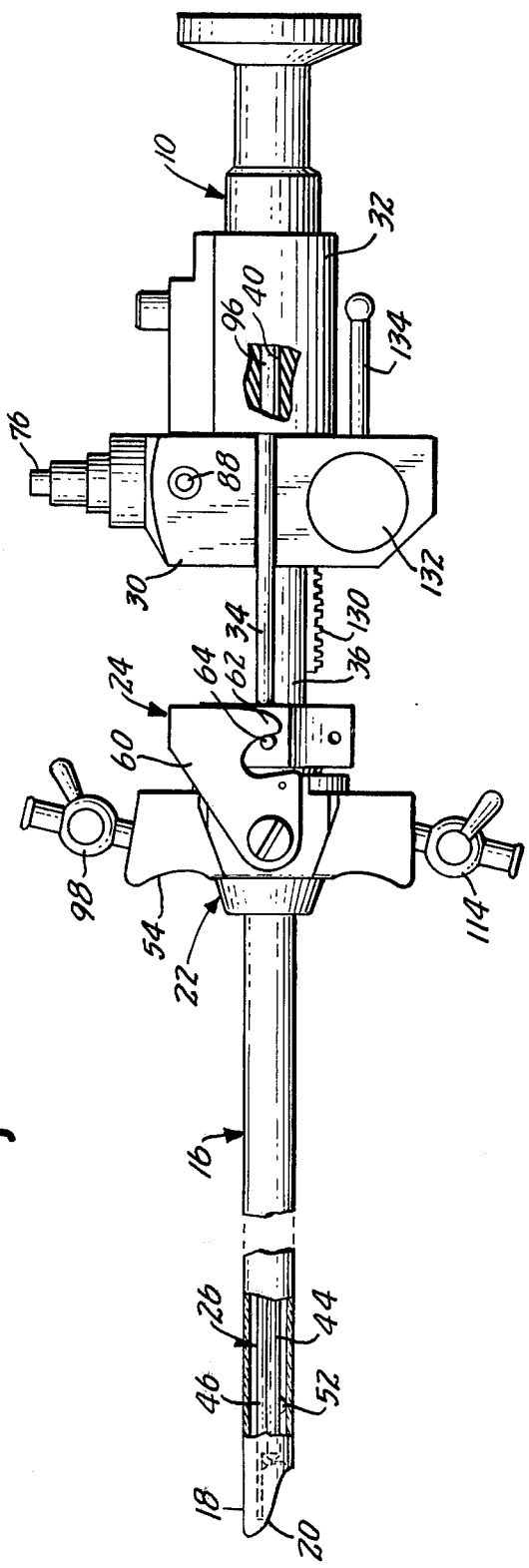
FIG. 4 is a vertical elevation view of the embodiment of FIG. 1 with a portion of the sheath cut away to show a supporting foot on the bottom of the working element stem.

Referring now to FIGS. 1 through 5 & 7–9 of the drawings, the preferred embodiment of a resectoscope according to the invention includes a telescope 10, having an eyepiece 11, an insulated tungsten cutting electrode 12, a working element assembly 14 and a dielectric sheath 16 made of conventional known material. The distal, or forward, end 18 of the sheath has its lower portion cut away to form a window or fenestra 20 through which the doctor views the area of interest and through which the electrode 12 operates. The sheath above the fenestra holds tissue above that portion from falling into the field of view or against the electrode. The proximal, or rearward, end 17 (FIG. 9) of the sheath 16 is mounted in the dielectric female cone block 22 which carries a conventional sheath locking mechanism 24 for connecting the sheath to the working element assembly portion 14 of the resectoscope.

The working element assembly 14 includes a stainless steel thin wall stem 26, a dielectric cone portion 28, a movable dielectric block 30, a dielectric end block 32, a pair of metal rails covered with insulation 34 and a curved dielectric bridge 36. The rails 34 are spaced apart and rigidly connect the block 32 to the cone portion 28. The bridge 36 forms an upwardly facing trough between the rails 34 and likewise connects the cone portion 28 with the end block. The movable block 30 contains openings through it enabling the block to slide back and forth over the rails and bridge. The movable block 30 & end block 32 also include channels 38 & 40 (FIGS. 10 & 4) respectively through which the telescope 10 is inserted over the bridge 36 into the working element stem portion of the instrument. A similar channel for the telescope through the cone portion 28 is not shown.

Figure 5:
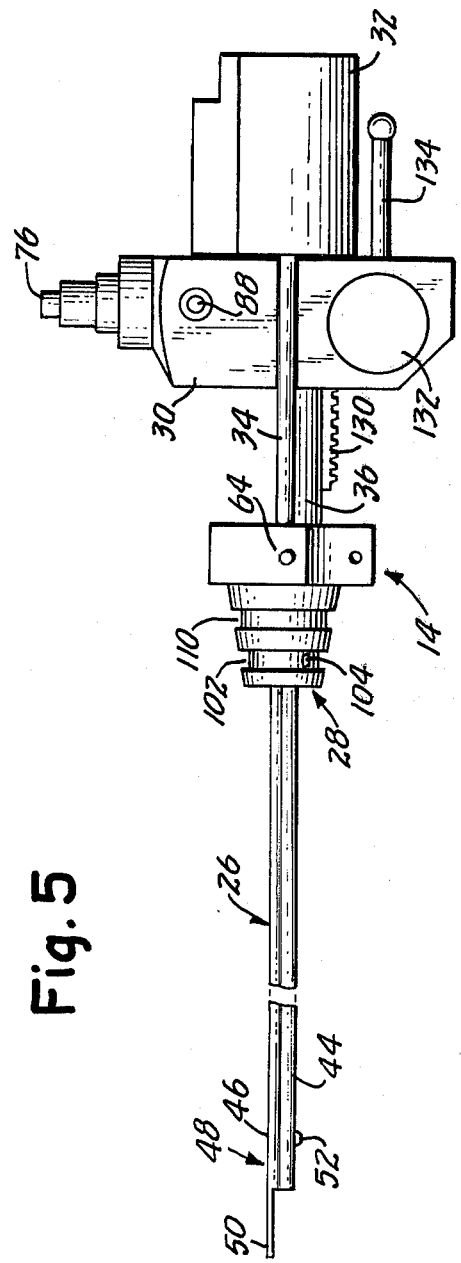
FIG. 5 is a vertical elevation view of the working element assembly of FIG. 1.

The stem portion 26 of the working element assembly is mounted in the cone 28 by a metal collar 42 and includes tubular cutting electrode channel members 46 sealingly mounted on a tubular telescope channel 44 member along its length. Preferably the guide channel members 46 are soldered or otherwise mounted on opposite sides of the upper portion of the stem and form what look like mouse ears on the stem when seen in cross section, (FIG. 7). Further, as best seen in FIGS. 2, 5 & 8, the lower portion of the distal end 48 of the stem 26 is cut away leaving the upper portions of the guide channel members 46 and the upper portion of the telescope channel member 44 between them defining a cantilevered roof 50. The guide channel member portions of this roof seal against both the sheath and the telescope channel member and project forward of the distal end of the telescope. A pair of openings 51 are formed in the roof 50 adjacent the front end of the telescope 10. When the upper conduit is used for drainage of irrigation fluid this enables bubbles formed during operation of the instrument to be drawn into the drain conduit above the roof.

In addition, as seen in FIGS. 2 & 8, there is a member 53 mounted on the distal end of the roof 50. This member extends generally upwardly and is rounded to fit the curvature of but be spaced away from the upper inside wall of the sheath 16. Further, this member has a plurality of openings or slots 55 distributed over its surface so that irrigation fluid will flow into the conduit through at least some of these openings even if others become clogged by pieces of tissue during resection. The sheath 16 also preferably includes a plurality of openings 57 proximally adjacent the member 53 and above the roof 50 to facilitate drainage. The member 53 may be fixed to the roof as shown or formed from an extended portion of the roof and bent upwardly toward the sheath. This latter form may be preferable in certain circumstances.

On the bottom of the working element stem 26, within the sheath and spaced a distance rearwardly of the roof 50 is a metallic foot 52 which supports the distal or forward end of the stem upwardly in the sheath 16 to ensure a good seal between the guide channel members 46 of the stem and the sheath.

Referring now to FIGS. 1, 4 & 9, the female cone block 22 has curved portions 54 above and below the sheath 16. The block 22 includes a conical cavity 56 in which the cone portion 28 of the working element assembly 14 nests when the sheath 16 is connected to the assembly. The sheath connection locking mechanism 24 includes a dielectric U-shaped member 58 pivotally mounted about the ends of its arms 60 on opposite sides of the block 22 and has a pair of locking pawls 62 which engage a pair of projecting pins 64 on the distal ends of the rails 34 on opposite sides of the block 22 to hold the block and sheath on the working element assembly 14. Preferably, the U-shaped member 58 is spring biased downwardly by a spring to maintain a locking condition between the block and cone.

The preferred embodiment of the cutting electrode 12 includes a loop 68 at the distal end of the electrode and a pair of substantially parallel spaced apart arms 69 extending rearwardly from the loop in the same direction. The distal portions of these arms are reinforced to give added strength to the loop (if the wire is not sufficiently rigid). The reinforcement preferably comprises stiffening elements 70 such as metal sleeves which extend from the loop 68 rearwardly a distance which is greater than the length of travel of the electrode 12 when reciprocated back and forth in the instrument. Normally, this length is about 25 mm. or more. The entire electrode 12 from the ends of the loop 68 to the free ends 71 of the arms 69 is covered with a layer of electrical insulation material 73 at least about 0.015 inches thick to isolate the guide channel members 46 of the stem 26 from the electrode wire 72 itself when the electrode is inserted into these members. If desired the stiffening elements 70 may surround the insulation rather than lie beneath as shown in FIG. 3. Preferably, the free ends 71 of the arms 69 have snap-in quick release male terminals 74 connected to them for easy electrical connection with the release from the active wire 76 which feeds electrical power into the block 30.

Referring now to FIGS. 1, 10 & 14, an insulated active wire 76 enters the block 30 from the top and connects electrically to a downwardly spring biased electrode 78 which is slidable within a brass sleeve 79. The electrode has a pair of conducting pins 80 projecting downwardly into a pair of transverse channels 81 in the sleeve 79 for receiving the free ends 71 of the arms 69. The electrode also includes a sideway 84 which cooperates with a spring biased dielectric cam member 86 having a finger operated portion 88 extending outwardly of the block. In operation, when the finger operated portion 88 is pushed into the block against the force of its biasing spring 90 it moves through the slideway 84 and raises the electrode 78 against the force of its biasing spring 92 thus disengaging the pins 80 from the male terminals 74. When the finger operated portion 88 is released, the pins 80 descend again to their bottom position. In this position (shown in FIG. 14) they can be raised out of the way slightly on urging the male terminals into engaged position and will automatically snap back to engage the grooves 94 in these terminals when the electrode arms are fully seated in the block 30. The channels 81 in the block 30 are tapered slightly at the entrance to the block to facilitate insertion of the terminals and slope upwardly from this entrance as they penetrate the block away from the telescope 44. This causes the terminals 74 in the middle of the block to engage the pins 80 at a point above the telescope channel. As already indicated the terminals and contacting conductors should be at least about 0.03 inches away from this channel and preferably not less than about 0.06 inches from it.

When preparing the resectoscope for use, the cutting electrode 12 is inserted into the working element assembly 14 by placing the male terminal of each arm 69 in the front end of its guide channel member 46 and pushing the electrode rearwardly until the arms 69 emerge from the corresponding channels at the rear of the cone portion of the working element assembly. From there the arms 69 pass above the bridge over the telescope shaft 96 and into the channels 81 in the block 30. Terminals 74 then move upwardly and rearwardly finally becoming connected with the pins 80.

Though, preferably, the guide channel members 46 comprise tubes mounted on the telescope channel member 44, in resectoscopes in which the interior space within the sheath is not large enough to accommodate the wall thickness involved in such a structure, the telescope channel member and guide channel members may be formed from a single metal tube in which the guide channel members protrude radially from the telescope channel member and are open inwardly to it along their lengths.

Referring now to FIGS. 1 & 9, if desired the irrigation fluid may flow into the resectoscope through a conventional metal valve 98 in the upper portion of the finger grip block 22. From there it can flow through a channel 100 in the block into an annular groove 102 in the forward portion of the cone 28. From there it may pass through a radially inward opening 104 in the groove 102 and stem collar 42 forwardly between the sheath and the lower portion of the telescope channel 44 to the fenestra 20. A rectangular gasket 106 is provided around the stem 26 at the front of the cone 28 to form a seal between the sheath 16 and the collar 42. In the preferred embodiment, this gasket also seals against the guide channel members 46 of the stem 26 and in this way keeps the fluid below the guide channel portions 46 of the stem 26 separate from that above them. If desired, the draining fluid may pass rearwardly between the stem 26 and the collar 42 and then upwardly through a radially outwardly extending opening 108 in the collar 42 and cone 28 to an annular groove 110 in the cone. From there it may flow downwardly around the grove into a channel 112 in the lower portion of block 22 and out through a conventional metal valve 114.

The operation of the resectoscope according to the invention is conventional and in the preferred embodiment shown in the drawings uses a rack and pinion mechanism for moving the block 30 forward and back. A dielectric rack 130 is attached to the bottom of the bridge 36 and the pinion (not shown) is mounted on a dielectric shaft 132 through a horizontal opening through the block 30. A channel in the block (not shown) permits the block to move forwardly and back over the rack 130. A dielectric lever arm 134 is mounted on a dielectric knob 136 at one end of the shaft 132 (see FIG. 6) to rotate the shaft. The teeth on the rack and pinion mesh together so about a 180° turn of the shaft moves the block all the way forward or back. As the block moves, it drives the electrode arms 69 through the cone 28, block 22 and guide channels 46. The loop 68 is thereby moved forward and back along its path of travel in front of the telescope 10. The path of travel of the loop 68 extends from a couple of millimeters within the sheath to about 25 millimeters forwardly of the lower lip of the fenestra 20.

In the resectoscope according to the preferred embodiment of the invention, when the electrode 12 is in its forward position, its loop portion 68 is supported by its reinforced sections 70 in the guide channels 46 against lateral or upward movement. When in its rearward or retracted position, the loop portion 68 lies above the bottom portion of the sheath 16 and in front of the distal end of the telescope 10. It is also held in this position by the reinforced portions 70 of the electrode 12 in the guide channel members 46 so that the loop 68 will not contact the sheath 16 or the telescope 10. As indicated previously, the telescope shaft 96 is isolated electrically from all other conductive material at the ground or patient plate potential. Accordingly, even if it should be touched by the electrode the resulting effect would be minimal and no harm should be done to the telescope.

Referring now to FIG. 11 of the drawings, a second embodiment of the working element stem portion 26a of the resectoscope according to the invention will be described. The use of alphabetical letters in connection with numbers for certain parts in this specification and in the drawings is to identify the parts which are the same in each of the various different embodiments. The stem 26a includes a telescope channel member 44a and electrode guide channel members 46a as in the preferred embodiment but, instead of having these guide channel members seal directly against the sheath 16a, as in the preferred embodiment, a cover 138 is provided which seals against the guide channel members 46a on one side and nests snugly against the sheath 16a on the other. This cover 138 extends the length of the stem 26 including the portion of it forming the roof 50a. This cover includes at least one slot or other opening (not shown) adjacent the drainage openings 57 in the sheath (see FIGS. 2 & 8) to facilitate the passage of irrigation fluid into the drainage conduit. In all other respects this second stem embodiment is like that of the preferred embodiment.

Referring to FIG. 12, a third embodiment of a working element stem 26b according to the invention includes telescope channel and electrode guide channel members 44b and 46b respectively, but instead of a cover as in the second embodiment it includes an enclosed drainage conduit 140 which is mounted on the upper side of the stem 26b, nesting between the guide channel members 46b and fitting against the sheath 16b at its upper surface. In this embodiment as in the second, the guide channel members 46b of the stem do not sealingly engage the sheath 16b. Similarly, the conduit 140 extends the length of the stem including the roof portion 56b and has the same slots or other drainage openings (not shown) referred to above in connection with the second stem embodiment.

Turning finally to FIG. 13, a second embodiment of an electrode 12a according to the invention comprises the same electrode as the preferred embodiment, but without the reinforcement portion at the distal end of the electrode. Thus, it includes a loop 68a, arms 69a, wire 72a, insulation 73a and male terminals 74a at its free ends 71a.

While various embodiments of the invention have been described in the foregoing specification, it will be understood that various modifications may be made to these embodiments within the scope of the invention as defined by the appended claims.

What is claimed is:

1. A working element assembly for use in a resectoscope having a sheath, said assembly including a stem portion for insertion within the sheath, and having a telescope channel member with a central axis and a pair of parallel cutting electrode guide channel members spaced apart and sealingly mounted on the telescope channel member on opposite sides thereof substantially along its full length above its central axis and in which a portion of the cutting electrode guide channel members and the telescope channel member portion between them and above said axis form a roof member which extends a distance distally beyond the portion of the telescope channel member below said axis.

2. A stem for a working element assembly for use in a resectoscope, the stem having a telescope channel member along its length with a central axis and a pair of parallel cutting electrode channel members spaced apart and sealingly mounted on the telescope channel member on opposite sides thereof substantially along its full length above its central axis and in which a portion of the cutting electrode guide channel members and the telescope channel member portion between them and above said axis form a roof member which extends a distance distally beyond the portion of the telescope channel member below said axis.

3. In a resectoscope having a sheath and a working element assembly including a stem portion having a telescope channel member for insertion within the sheath, said member having a central axis, an irrigation fluid inflow conduit and an irrigation fluid drain conduit, both also within the sheath, the improvement in which the stem portion of the assembly includes a pair of substantially parallel spaced apart cutting electrode guide channel members sealingly mounted on the telescope channel member on opposite sides thereof substantially along its full length above its central axis.

4. The improvement according to claim 3 in which the cutting electrode guide channel members sealingly engage the telescope channel member and sealingly engage the sheath above said axis to partition the space between the sheath and the working element stem into said irrigation fluid drain and inflow conduits, one of which lies above and between said guide channel members and the other below and between them, and in which said electrode guide channel members also have a snug yet slidable relationship with the sheath to permit insertion and removal of the stem into and out of the sheath.

5. In a resectoscope according to claim 4 the improvement wherein there is a foot member mounted on the lower portion of the stem a distance rearwardly of its distal end in contact with the sheath for spacing the stem's lower portion a predetermined distance away from the lower portion of the sheath and for urging the electrode guide channel members into said sealing, snug yet slidable relationship with the sheath.

6. The improvement according to claim 4 wherein the telescope channel member has a portion adjacent the bottom of the sheath, there is a foot member mounted on said telescope channel member portion for spacing said portion a predetermined distance away from the bottom of the sheath and for causing the electrode guide channel members to engage upper portions of the sheath in a snug yet slidable relationship and the stem has an upper portion comprising a roof which extends a distance distally of said telescope channel member portion adjacent the bottom of the sheath for extending one of the irrigation fluid conduits distally of the other.

7. The improvement according to claim 3 in which a separate conduit member is fixedly mounted on the stem along the length of its telescope channel member, said conduit member having a snug yet slidable relation with the sheath, defining one of the two irrigation fluid flow conduits and having a cross sectional area which maximizes fluid flow through the conduit.

8. The improvement according to claim 3 in which one of the conduits is defined by a cover which lies over the telescope channel member, in a snug but slidable relationship against the sheath and sealingly engages the cutting electrode guide channel members adjacent the sheath.

9. In a resectoscope according to claim 3, wherein the stem and sheath have upper and lower portions, the improvement comprising a foot member mounted on the lower portion of the stem in contact with the lower portion of the sheath for urging the upper portion of the stem against the upper portion of the sheath into a snug yet slidable relation therewith.

10. In a resectoscope having a sheath and a working element assembly including a stem portion having a telescope channel member for insertion within the sheath, said member having a central axis, an irrigation fluid inflow conduit and an irrigation fluid drain conduit, both also within the sheath the improvement in which the stem portion of the assembly includes a pair of substantially parallel spaced apart cutting electrode guide channel members sealingly mounted on the telescope channel member on opposite sides thereof substantially along its full length above its central axis and in which a portion of the cutting electrode guide channel members and the telescope channel member portion between them and above said axis form a roof member which extends a distance distally beyond the portion of the telescope channel member below said axis.

11. The improvement according to claim 10 wherein the roof member includes at least one aperture in its telescope channel member portion through which fluid can flow.

12. A cutting electrode for use in a working element assembly for use in a resectoscope having cutting electrode guide channel members on opposite sides of the working element above its central axis, said electrode consisting of a continuous unbranched length of an electrical conductor with an uninsulated loop portion in the middle of the conductor and a pair of similar, free, substantially straight, flexible, parallel, spaced apart insulation covered arms extending rearwardly from the loop in the same direction for the remaining length of the electrode, and means for connecting the electrical conductor to a source of electric current.

13. A cutting electrode according to claim 12 in which the arms beginning at the loop portion and extending a predetermined distance rearwardly from the loop are stiffer than the remaining portions of the arms to provide additional rigidity and support to the loop.

14. A cutting electrode according to claim 13 wherein the conductor portion of the arms are covered with stiffening elements under the insulation throughout the stiffer section of the electrode.

15. A cutting electrode according to claim 12 wherein the electric connecting means comprises quick disconnect electrical terminals on the ends of the electrode arms.

16. In a resectoscope having a metal working element stem and a cutting electrode reciprocatingly mounted within the stem, the improvement comprising having all other parts of the resectoscope which are exposed to contact by the operator using the instrument or the patient in which it is used formed, as far as possible, of dielectric material, having any necessary external parts which are capable of conducting electricity made as small as possible, having these external parts formed with a minimum of electrically conductive interconnections between them and having these parts spaced by a dielectric from those parts of the instrument intended to carry electricity to produce a capacitive coupling between them of less than about 6 pico farads and an ohmic coupling of not less than about 25,000 ohms.

17. A resectoscope according to claim 16 wherein the conductive surfaces are sufficiently small and the dielectric layer is of adequate thickness to result in an isolation capacitance of less than about 4 pico farads.

18. A resectoscope according to claim 16 in which there is also a telescope having a metal shaft within the working element stem and there is a dielectric material which isolates the telescope's shaft from the instrument's external conductive surfaces with a capacitive coupling of less than about 6 pico farads and a resistive coupling of more than about 25,000 ohms and there is dielectric material between the shaft and the electrode which does not break down under the electrical voltages and frequencies used.

19. A resectoscope according to claim 16 having a cutting electrode with at least one terminal, a telescope and a working element assembly with a moving block portion comprising a dielectric material, the block portion including at least one upwardly sloping channel for the cutting electrode and terminal, there being means in said block for connecting electricity to said terminal of said electrode in the channel, said means and terminal being located in said channel at least about 0.03 inches away from said telescope.

* * * * *

UNITED STATES PATENT OFFICE
CERTIFICATE OF CORRECTION

PATENT NO. : 3,939,839
DATED : February 24, 1976
INVENTOR(S) : Lawrence Curtiss

It is certified that error appears in the above-identified patent and that said Letters Patent are hereby corrected as shown below:

Col. 4, line 46 after "stem" insert --away--.

Col. 4, line 60 Delete "of".

Col. 5, line 67 "betwen" should be --between--.

Col. 7, line 24 change "the" (first occurrence) to --and--.

Signed and Sealed this

Twentieth Day of July 1976

[SEAL]

Attest:

RUTH C. MASON
*Attesting Officer*

C. MARSHALL DANN
*Commissioner of Patents and Trademarks*